United States Patent [19]
Johann et al.

[11] Patent Number: 5,550,221
[45] Date of Patent: Aug. 27, 1996

[54] NUCLEIC ACID MOLECULE ENCODING THE AMPHOTROPIC VIRUS RECEPTOR

[75] Inventors: Stephen V. Johann, Pearl River; Marja van Zeijl, Cornwall; Bryan M. O'Hara, Pearl River, all of N.Y.

[73] Assignee: American Cyanamid Company, Wayne, N.J.

[21] Appl. No.: 50,684

[22] Filed: Apr. 16, 1993

[51] Int. Cl.⁶ ............................ C12N 15/09; C07H 21/00; C07K 14/705
[52] U.S. Cl. ................... 536/23.5; 536/23.1; 435/69.1; 435/240.1; 435/252.3; 435/254.11; 435/320.1
[58] Field of Search ................. 536/23.1, 23.5; 435/69.1, 240.1, 320.1, 252.3, 254.11

[56] References Cited

PUBLICATIONS

Sommerfelt, MA et al, Receptor Interference Groups of 20 Retroviruses Plating on Human Cells, Virology, vol. 176, No. 1, pp. 58–69, 1990.

Handelin, B. L., et al., Cell Surface Receptors for Murine Leukemia Viruses: Two Assays and Their Implications, Virology, vol. 140, No. 1, pp. 183–187 (1985).

Kawakami, T. G., et al., Antiagenic Studies on Gibbon Type–C Viruses, Transplantation Proceedings, vol. VI, No. 2 (Jun.), pp. 193–196, 1974.

Kawakami, T. G., et al., Letters to Nature, Nature New Biology, vol. 235, pp. 170–171, (1972).

Kawakami, T. G., et al., Onocogenicity of Gibbon Type–C Myelogenous Leukemia Virus, Int. J. Cancer: 25, 641–646 (1980).

Sanger, F., et al., DNA sequencing with chain–terminating inhibitors, Proc. Natl. Acad Sco, USA, vol. 74, No. 12, pp. 5463–5467, 1977.

O'Hara, B., et al., Characterization of a Human Gene Conferring Sensitivity to Infection by Gibbon Ape Leukemia Virus, Cell Growth & Differentiation, vol. 1: 119–127, 1990.

Kaelbling, M. et al., Localization of the Human Gene Allowing Infection by Gibbon Ape Leukemia Virus to Human Chromosome Region 2q11–q14 and to the Homologous Region on Mouse Chromosome 2, Journal of Virology, vol. 65, No. 4, pp. 1743–1747 (1991).

Garcia, J. V., et al., Localization of the Amphotropic Murine Leukemia Virus Receptor Gene to the Pericentromeric Region of Human Chromosome 8, Journal of Virology, vol. 65, No. 11, pp. 6316–6319, 1991.

MacLeod et al., Mol. Cell. Biol., vol. 10, p. 3663, 1990.

*Primary Examiner*—Stephen G. Walsh
*Assistant Examiner*—Sally P. Teng
*Attorney, Agent, or Firm*—Karen A. Lowney; Joseph R. Robinson

[57] ABSTRACT

The present invention relates to an isolated nucleic acid fragment comprising a nucleic acid sequence coding for an amphotropic retrovirus receptor. This receptor is referred to as GLVR2 and has approximately 62% homology with the GLVR1 gene encoding Gibbon Ape Leukemia Virus (GALV) receptor. Differences in the type of retroviruses interacting with the receptors exist. The protein encoded by the GLVR2, cells transformed or transfected by the gene, and vectors containing the gene are also disclosed.

8 Claims, 3 Drawing Sheets

```
CAGATCGGGA AGAAAAATAT GGAATGTGTT TTACCGCTGA CTGAACACAA CCAAATGAAC    60
TGTCCTGACA GTAGTTTGCA AACCAGCAGC TAGCAGTTTG TCCAGCCTCT AACATTGTCC   120
AGCACTTTCC AGAGCAAACT CACTGTTTAC AAGAACTCTT GGCCTTACGA AGTTTATAAC   180
CTCAAGCTTT GTTTATTTAA AATATTCCTG CAAAAGAAAA GTACCCGGCA CCCACTTTCC   240
AAAATGGCCA TGGATGAGTA TTTGTGGATG GTCATTTTGG GTTTCATCAT AGCTTTCATC   300
TTGGCCTTTT CTGTTGGTGC AAACGATGTT GCCAACTCCT TTGGTACAGC CGTGGGCTCT   360
GGTGTGGTGA CCTTGAGGCA GGCATGCATT TTAGCTTCAA TATTTGAAAC CACCGGCTCC   420
GTGTTACTAG GCGCCAAAGT AGGAGAAACC ATTCGCAAAG GTATCATTGA CGTGAACCTG   480
TACAACGAGA CGGTGGAGAC TCTCATGGCT GGGGAAGTTA GTGCCATGGT TGGTTCCGCT   540
GTGTGGCAGC TGATTGCTTC CTTCCTGAGG CTTCCAATCT CAGGAACGCA CTGCATTGTG   600
GGTTCTACTA TAGGATTCTC ACTGGTCGCA ATCGGTACCA AAGGTGTGCA GTGGATGGAG   660
CTTGTCAAGA TTGTTGCTTC TTGGTTTATA TCTCCACTGT TGTCTGGTTT CATGTCTGGC   720
CTGCTGTTTG TACTCATCAG AATTTTCATC TTAAAAAAGG AAGACCCTGT TCCCAATGGC   780
CTCCGGGCAC TCCCAGTATT CTATGCTGCT ACCATAGCAA TCAATGTCTT TTCCATCATG   840
TACACAGGAG CACCAGTGCT CGGCCTTGTT CTCCCCATGT GGGCCATAGC CCTCATTTCC   900
TTTGGTGTCG CCCTCCTGTT CGCTTTTTTT GTGTGGCTCT TCGTGTGTCC GTGGATGCGG   960
AGGAAAATAA CAGGCAAATT ACAAAAAGAA GGTGCTTTAT CACGAGTATC TGACGAAAGC  1020
CTCAGTAAGG TTCAGGAAGC AGAGTCCCCA GTATTTAAAG AGCTACCAGG TGCCAAGGCT  1080
AATGATGACA GCACCATCCC GCTCACGGGA GCAGCAGGGG AGACACTGGG GACCTCGGAA  1140
GGCACTTCTG CGGGCAGCCA CCCTCGGGCT GCATACGGAA GAGCACTGTC CATGACCCAT  1200
GGCTCTGTGA AATCGCCCAT CTCCAACGGC ACCTTCGGCT TCGACGGCCA CACCAGGAGC  1260
GACGGTCATG TGTACCACAC CGTGCACAAA GACTCGGGGC TCTACAAAGA TCTGCTGCAC  1320
AAAATCCACA TCGACAGGGG CCCCGAGGAG AAGCCAGCCC AGGAAAGCAA CTACCGGCTG  1380
CTCCGCCGAA ACAACAGTTA CACCTGCTAC ACCGCAGCCA TTTGTGGGCT GCCAGTGCAC  1440
GCCACCTTTC GAGCTGCGGA CTCATCGGCC CCAGAGGACA GTGAGAAGCT GGTGGGCGAC  1500
ACCGTGTCCT ACTCCAAGAA GAGGCTGCGC TACGACAGCT ACTCGAGCTA CTGTAACGCG  1560
GTGGCAGAGG CGGAGATCGA GGCGGAGGAG GGCGGCGTGG AGATGAAGCT GGCGTCGGAG  1620
CTGGCCGACC CTGACCAGCC GCGAGAGGAC CCTGCAGAGG AGGAGAAGGA GGAGAAGGAC  1680
GCACCCGAGG TTCACCTCCT GTTCCATTTC CTGCAGGTCC TCACCGCCTG TTTCGGGTCC  1740
TTTGCTCACG GCGGCAATGA CGTGAGTAAT GCCATCGGTC CCTGGTAGC CTTGTGGCTG  1800
ATTTACAAAC AAGGCGGGGT AACGCAAGAA GCAGCTACAC CCGTCTGGCT GCTGTTTTAT  1860
GGAGGAGTTG GAATCTGCAC AGGCCTCTGG GTCTGGGGGA GAAGAGTGAT CCAGACCATG  1920
GGGAAGGACC TCACTCCCAT CACGCCGTCC AGCGGCTTCA CGATCGAGCT GGCCTCAGCC  1980
TTCACAGTGG TGATCGCCTC CAACATCGGG CTTCCAGTCA GCACCACGCA CTGTAAGGTG  2040
```

FIG.1A

```
GGCTCGGTGG TGGCCGTGGG CTGGATCCGC TCCCGCAAGG CTGTGGACTG GCGCCTCTTT 2100
CGGAACATCT TCGTGGCCTG GTTCGTGACC GTCCCTGTGG CTGGGCTGTT CAGCGCTGCT 2160
GTCATGGCTC TTCTCATGTA TGGGATCCTT CCATATGTGT GATTTGTCTT CTTCCAGCTG 2220
CAAACAGCTA AAGGGATGGT CTGGTGTTGG CGTGTGGGAG ACATGTGTGC TCGTGCCGCA 2280
CATACACATC CTGGCCGTGC ACGGCTCTCT CATGACCAGC TCTCTGCCTC CCTTCCAGGA 2340
GGCTCCATCC CACACTGTTC ACCCAGGCTG CGGAGACTCA CCTTCCCGAG CTAACTTAAC 2400
TACTGTACAT AATAATATGT ATTAAACTGG TATCGTGGTG ATATAATGTG GTGCAGTTAC 2460
TTATATATTA AATATCTATT GTATCCATAG AATAGGCAGC ATTATTTCAA ACATATTCAA 2520
GTTGGGAGTG GAGATCATTG CCTAGAAGTC AATATTCAAT AAATCTTGTA CATAACTATT 2580
TCGATGGCAA ATGTTAAGCC TTCTAAAAGG AAAGTGTAGA TTGGAAAATG ATTTTTTTTC 2640
CAAATGATGT TTTTGCCTTC TAATATACTG TAAGGTAATG AGCTTCAGAA CAGGCAACCT 2700
GACCCTGCAG AGGTCGCGTG CTGTGGGATG ACAGCGGGAC GGGAGCTCAC AAGTGCTTTC 2760
ACTGAAGATT TGTTCATATA CTGTGTATTG ATTGTTGTGT AATATATCAT CATTGCTTTT 2820
GTAAATACGT AAAACTGTAA TTTTTTAATG GTGTGCTTCC CTTATACTTT TTGATCAGAG 2880
AATTTTGGAA AGTACCAAAG AAGCAGGGGA ATCATTGGCC AGTGTTACGT TTTCACATTG 2940
TCTGTCTCCC ACCCTCACTG ATCACGCCTG CCCCAGAGCA GTGTGTGGCG GTGACACCGT 3000
CACCCAGCAT GCGCCACGCC GTCGTCCCAC CAGCAGTGCC ACCGCCACCA CACCCCAGAT 3060
CCCACCCACC TTGCAGTGGC TTTCTTGTCA TCAGAGTAGA GAATGCACAG GTGTTGGTGA 3120
GGGCGTGTGG CTGAGCACTA CATGTCAAGT CAGAGTCAGT TTCTATCCAA TTCTC       3175
```

FIG.1B

```
MAMDEYLWMVILGFIIAFILAFSVGANDVANSFGTAVGSGVVTLRQACILASIFETTGSV   60

LLGAKVGETIRKGIIDVNLYNETVETLMAGEVSAMVGSAYWQLIASFLRLPISGTHCIVG  120

STIGFSLVAIGTKGVQWMELVKIVASWFISPLLSGFMSGLLFVLIRIFILKKEDPVPNGL  180

RALPVFYAATIAINVFSIMYTGAPVLGLVLPMWAIALISFGVALLFAFFVWLFVCPWMRR  240

KITGKLQKEGALSRVSDESLSKVQEAESPYFKELPGAKANDDSTIPLTGAAGETLGTSEG  300

TSAGSHPRAAYGRALSMTHGSVKSPISNGTFGFDGHTRSDGHVYHTVHKDSGLYKDLLHK  360

IHIDRGPEEKPAQESNYRLLRRNNSYTCYTAAICGLPVHATFRAADSSAPEDSEKLVGDT  420

VSYSKKRLRYDSYSSYCNAVAEAEIEAEEGGVEMKLASELADPDQPREDPAEEEKEEKDA  480

PEVHLLFHFLQVLTACFGSFAHGGNDVSNAIGPLVALVLIYKQGGVTQEAATPVWLLFYG  540

GVGICTGLVVWGRRVIQTMGKDLTPITPSSGFTIELASAFTYVIASNIGLPVSTTHCKVG  600

SVVAVGWIRSRKAVDWRLFRNIFVAWFVTVPVAGLFSAAVMALLMYGILPYV.         652
```

FIG.2

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 3175 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
    ( A ) NAME/KEY: CDS
    ( B ) LOCATION: 244..2202

( x i ) SEQUENCE DESCRIPTION: SEQ ID NO:1:

```
CAGATCGGGA AGAAAAATAT GGAATGTGTT TTACCGCTGA CTGAACACAA CCAAATGAAC        60

TGTCCTGACA GTAGTTTGCA AACCAGCAGC TAGCAGTTTG TCCAGCCTCT AACATTGTCC       120

AGCACTTTCC AGAGCAAACT CACTGTTTAC AAGAACTCTT GGCCTTACGA AGTTTATAAC       180

CTCAAGCTTT GTTTATTTAA AATATTCCTG CAAAAGAAAA GTACCGGCA CCCACTTTCC        240

AAA ATG GCC ATG GAT GAG TAT TTG TGG ATG GTC ATT TTG GGT TTC ATC     288
        Met Ala Met Asp Glu Tyr Leu Trp Met Val Ile Leu Gly Phe Ile
          1               5                  10                  15

ATA GCT TTC ATC TTG GCC TTT TCT GTT GGT GCA AAC GAT GTT GCC AAC     336
    Ile Ala Phe Ile Leu Ala Phe Ser Val Gly Ala Asn Asp Val Ala Asn
                       20                  25                  30

TCC TTT GGT ACA GCC GTG GGC TCT GGT GTG GTG ACC TTG AGG CAG GCA     384
    Ser Phe Gly Thr Ala Val Gly Ser Gly Val Val Thr Leu Arg Gln Ala
                   35                  40                  45

TGC ATT TTA GCT TCA ATA TTT GAA ACC ACC GGC TCC GTG TTA CTA GGC     432
    Cys Ile Leu Ala Ser Ile Phe Glu Thr Thr Gly Ser Val Leu Leu Gly
               50                  55                  60

GCC AAA GTA GGA GAA ACC ATT CGC AAA GGT ATC ATT GAC GTG AAC CTG     480
    Ala Lys Val Gly Glu Thr Ile Arg Lys Gly Ile Ile Asp Val Asn Leu
           65                  70                  75

TAC AAC GAG ACG GTG GAG ACT CTC ATG GCT GGG GAA GTT AGT GCC ATG     528
    Tyr Asn Glu Thr Val Glu Thr Leu Met Ala Gly Glu Val Ser Ala Met
     80                  85                  90                  95

GTT GGT TCC GCT GTG TGG CAG CTG ATT GCT TCC TTC CTG AGG CTT CCA     576
    Val Gly Ser Ala Val Trp Gln Leu Ile Ala Ser Phe Leu Arg Leu Pro
                       100                 105                 110

ATC TCA GGA ACG CAC TGC ATT GTG GGT TCT ACT ATA GGA TTC TCA CTG     624
    Ile Ser Gly Thr His Cys Ile Val Gly Ser Thr Ile Gly Phe Ser Leu
                   115                 120                 125

GTC GCA ATC GGT ACC AAA GGT GTG CAG TGG ATG GAG CTT GTC AAG ATT     672
    Val Ala Ile Gly Thr Lys Gly Val Gln Trp Met Glu Leu Val Lys Ile
               130                 135                 140

GTT GCT TCT TGG TTT ATA TCT CCA CTG TTG TCT GGT TTC ATG TCT GGC     720
    Val Ala Ser Trp Phe Ile Ser Pro Leu Leu Ser Gly Phe Met Ser Gly
           145                 150                 155

CTG CTG TTT GTA CTC ATC AGA ATT TTC ATC TTA AAA AAG GAA GAC CCT     768
    Leu Leu Phe Val Leu Ile Arg Ile Phe Ile Leu Lys Lys Glu Asp Pro
    160                 165                 170                 175

GTT CCC AAT GGC CTC CGG GCA CTC CCA GTA TTC TAT GCT GCT ACC ATA     816
    Val Pro Asn Gly Leu Arg Ala Leu Pro Val Phe Tyr Ala Ala Thr Ile
                       180                 185                 190

GCA ATC AAT GTC TTT TCC ATC ATG TAC ACA GGA GCA CCA GTG CTC GGC     864
    Ala Ile Asn Val Phe Ser Ile Met Tyr Thr Gly Ala Pro Val Leu Gly
                   195                 200                 205

CTT GTT CTC CCC ATG TGG GCC ATA GCC CTC ATT TCC TTT GGT GTC GCC     912
    Leu Val Leu Pro Met Trp Ala Ile Ala Leu Ile Ser Phe Gly Val Ala
               210                 215                 220

CTC CTG TTC GCT TTT TTT GTG TGG CTC TTC GTG TGT CCG TGG ATG CGG     960
    Leu Leu Phe Ala Phe Phe Val Trp Leu Phe Val Cys Pro Trp Met Arg
           225                 230                 235

AGG AAA ATA ACA GGC AAA TTA CAA AAA GAA GGT GCT TTA TCA CGA GTA    1008
    Arg Lys Ile Thr Gly Lys Leu Gln Lys Glu Gly Ala Leu Ser Arg Val
    240                 245                 250                 255

TCT GAC GAA AGC CTC AGT AAG GTT CAG GAA GCA GAG TCC CCA GTA TTT    1056
```

```
                    Ser  Asp  Glu  Ser  Leu  Ser  Lys  Val  Gln  Glu  Ala  Glu  Ser  Pro  Val  Phe
                                        260                      265                     270

AAA  GAG  CTA  CCA  GGT  GCC  AAG  GCT  AAT  GAT  GAC  AGC  ACC  ATC  CCG  CTC                      1104
Lys  Glu  Leu  Pro  Gly  Ala  Lys  Ala  Asn  Asp  Asp  Ser  Thr  Ile  Pro  Leu
               275                     280                     285

ACG  GGA  GCA  GCA  GGG  GAG  ACA  CTG  GGG  ACC  TCG  GAA  GGC  ACT  TCT  GCG                      1152
Thr  Gly  Ala  Ala  Gly  Glu  Thr  Leu  Gly  Thr  Ser  Glu  Gly  Thr  Ser  Ala
               290                     295                     300

GGC  AGC  CAC  CCT  CGG  GCT  GCA  TAC  GGA  AGA  GCA  CTG  TCC  ATG  ACC  CAT                      1200
Gly  Ser  His  Pro  Arg  Ala  Ala  Tyr  Gly  Arg  Ala  Leu  Ser  Met  Thr  His
          305                      310                     315

GGC  TCT  GTG  AAA  TCG  CCC  ATC  TCC  AAC  GGC  ACC  TTC  GGC  TTC  GAC  GGC                      1248
Gly  Ser  Val  Lys  Ser  Pro  Ile  Ser  Asn  Gly  Thr  Phe  Gly  Phe  Asp  Gly
320                      325                     330                          335

CAC  ACC  AGG  AGC  GAC  GGT  CAT  GTG  TAC  CAC  ACC  GTG  CAC  AAA  GAC  TCG                      1296
His  Thr  Arg  Ser  Asp  Gly  His  Val  Tyr  His  Thr  Val  His  Lys  Asp  Ser
                    340                     345                     350

GGG  CTC  TAC  AAA  GAT  CTG  CTG  CAC  AAA  ATC  CAC  ATC  GAC  AGG  GGC  CCC                      1344
Gly  Leu  Tyr  Lys  Asp  Leu  Leu  His  Lys  Ile  His  Ile  Asp  Arg  Gly  Pro
               355                     360                     365

GAG  GAG  AAG  CCA  GCC  CAG  GAA  AGC  AAC  TAC  CGG  CTG  CTC  CGC  CGA  AAC                      1392
Glu  Glu  Lys  Pro  Ala  Gln  Glu  Ser  Asn  Tyr  Arg  Leu  Leu  Arg  Arg  Asn
               370                     ·375                    380

AAC  AGT  TAC  ACC  TGC  TAC  ACC  GCA  GCC  ATT  TGT  GGG  CTG  CCA  GTG  CAC                      1440
Asn  Ser  Tyr  Thr  Cys  Tyr  Thr  Ala  Ala  Ile  Cys  Gly  Leu  Pro  Val  His
          385                     390                      395

GCC  ACC  TTT  CGA  GCT  GCG  GAC  TCA  TCG  GCC  CCA  GAG  GAC  AGT  GAG  AAG                      1488
Ala  Thr  Phe  Arg  Ala  Ala  Asp  Ser  Ser  Ala  Pro  Glu  Asp  Ser  Glu  Lys
400                      405                     410                          415

CTG  GTG  GGC  GAC  ACC  GTG  TCC  TAC  TCC  AAG  AAG  AGG  CTG  CGC  TAC  GAC                      1536
Leu  Val  Gly  Asp  Thr  Val  Ser  Tyr  Ser  Lys  Lys  Arg  Leu  Arg  Tyr  Asp
                    420                     425                     430

AGC  TAC  TCG  AGC  TAC  TGT  AAC  GCG  GTG  GCA  GAG  GCG  GAG  ATC  GAG  GCG                      1584
Ser  Tyr  Ser  Ser  Tyr  Cys  Asn  Ala  Val  Ala  Glu  Ala  Glu  Ile  Glu  Ala
               435                     440                     445

GAG  GAG  GGC  GGC  GTG  GAG  ATG  AAG  CTG  GCG  TCG  GAG  CTG  GCC  GAC  CCT                      1632
Glu  Glu  Gly  Gly  Val  Glu  Met  Lys  Leu  Ala  Ser  Glu  Leu  Ala  Asp  Pro
               450                     455                     460

GAC  CAG  CCG  CGA  GAG  GAC  CCT  GCA  GAG  GAG  GAG  AAG  GAG  GAG  AAG  GAC                      1680
Asp  Gln  Pro  Arg  Glu  Asp  Pro  Ala  Glu  Glu  Glu  Lys  Glu  Glu  Lys  Asp
          465                     470                      475

GCA  CCC  GAG  GTT  CAC  CTC  CTG  TTC  CAT  TTC  CTG  CAG  GTC  CTC  ACC  GCC                      1728
Ala  Pro  Glu  Val  His  Leu  Leu  Phe  His  Phe  Leu  Gln  Val  Leu  Thr  Ala
480                      485                     490                          495

TGT  TTC  GGG  TCC  TTT  GCT  CAC  GGC  GGC  AAT  GAC  GTG  AGT  AAT  GCC  ATC                      1776
Cys  Phe  Gly  Ser  Phe  Ala  His  Gly  Gly  Asn  Asp  Val  Ser  Asn  Ala  Ile
                    500                     505                     510

GGT  CCC  CTG  GTA  GCC  TTG  TGG  CTG  ATT  TAC  AAA  CAA  GGC  GGG  GTA  ACG                      1824
Gly  Pro  Leu  Val  Ala  Leu  Trp  Leu  Ile  Tyr  Lys  Gln  Gly  Gly  Val  Thr
               515                     520                     525

CAA  GAA  GCA  GCT  ACA  CCC  GTC  TGG  CTG  CTG  TTT  TAT  GGA  GGA  GTT  GGA                      1872
Gln  Glu  Ala  Ala  Thr  Pro  Val  Trp  Leu  Leu  Phe  Tyr  Gly  Gly  Val  Gly
               530                     535                     540

ATC  TGC  ACA  GGC  CTC  TGG  GTC  TGG  GGG  AGA  AGA  GTG  ATC  CAG  ACC  ATG                      1920
Ile  Cys  Thr  Gly  Leu  Trp  Val  Trp  Gly  Arg  Arg  Val  Ile  Gln  Thr  Met
     545                     550                      555

GGG  AAG  GAC  CTC  ACT  CCC  ATC  ACG  CCG  TCC  AGC  GGC  TTC  ACG  ATC  GAG                      1968
Gly  Lys  Asp  Leu  Thr  Pro  Ile  Thr  Pro  Ser  Ser  Gly  Phe  Thr  Ile  Glu
560                      565                     570                          575

CTG  GCC  TCA  GCC  TTC  ACA  GTG  GTG  ATC  GCC  TCC  AAC  ATC  GGG  CTT  CCA                      2016
```

|  |  |  |  |  |  |  |  |  |  |  |  |  |  |  |  |  |
|---|---|---|---|---|---|---|---|---|---|---|---|---|---|---|---|---|
| Leu | Ala | Ser | Ala | Phe 580 | Thr | Val | Val | Ile | Ala 585 | Ser | Asn | Ile | Gly | Leu 590 | Pro |  |
| GTC Val | AGC Ser | ACC Thr | ACG Thr | CAC His 595 | TGT Cys | AAG Lys | GTG Val | GGC Gly | TCG Ser 600 | GTG Val | GTG Val | GCC Ala | GTG Val | GGC Gly 605 | TGG Trp | 2064 |
| ATC Ile | CGC Arg | TCC Ser | CGC Arg 610 | AAG Lys | GCT Ala | GTG Val | GAC Asp | TGG Trp | CGC Arg 615 | CTC Leu | TTT Phe | CGG Arg | AAC Asn 620 | ATC Ile | TTC Phe | 2112 |
| GTG Val | GCC Ala | TGG Trp 625 | TTC Phe | GTG Val | ACC Thr | GTC Val 630 | CCT Pro | GTG Val | GCT Ala | GGG Gly | CTG Leu 635 | TTC Phe | AGC Ser | GCT Ala | GCT Ala | 2160 |
| GTC Val 640 | ATG Met | GCT Ala | CTT Leu | CTC Leu | ATG Met 645 | TAT Tyr | GGG Gly | ATC Ile | CTT Leu | CCA Pro 650 | TAT Tyr | GTG Val | TGATTTGTCT |  |  | 2209 |

```
TCTTCCAGCT GCAAACAGCT AAAGGGATGG TCTGGTGTTG GCGTGTGGGA GACATGTGTG    2269
CTCGTGCCGC ACATACACAT CCTGGCCGTG CACGGCTCTC TCATGACCAG CTCTCTGCCT    2329
CCCTTCCAGG AGGCTCCATC CCACACTGTT CACCCAGGCT GCGGAGACTC ACCTTCCCGA    2389
GCTAACTTAA CTACTGTACA TAATAATATG TATTAAACTG GTATCGTGGT GATATAATGT    2449
GGTGCAGTTA CTTATATATT AAATATCTAT TGTATCCATA GAATAGGCAG CATTATTTCA    2509
AACATATTCA AGTTGGGAGT GGAGATCATT GCCTAGAAGT CAATATTCAA TAAATCTTGT    2569
ACATAACTAT TTCGATGGCA AATGTTAAGC CTTCTAAAAG GAAAGTGTAG ATTGGAAAAT    2629
GATTTTTTTT CCAAATGATG TTTTTGCCTT CTAATATACT GTAAGGTAAT GAGCTTCAGA    2689
ACAGGCAACC TGACCCTGCA GAGGTCGCGT GCTGTGGGAT GACAGCGGGA CGGGAGCTCA    2749
CAAGTGCTTT CACTGAAGAT TTGTTCATAT ACTGTGTATT GATTGTTGTG TAATATATCA    2809
TCATTGCTTT TGTAAATACG TAAAACTGTA ATTTTTTAAT GGTGTGCTTC CCTTATACTT    2869
TTTGATCAGA GAATTTTGGA AAGTACCAAA GAAGCAGGGG AATCATTGGC CAGTGTTACG    2929
TTTTCACATT GTCTGTCTCC CACCCTCACT GATCACGCCT GCCCCAGAGC AGTGTGTGGC    2989
GGTGACACCG TCACCCAGCA TGCGCCACGC CGTCGTCCCA CCAGCAGTGC CACCGCCACC    3049
ACACCCCAGA TCCCACCCAC CTTGCAGTGG CTTTCTTGTC ATCAGAGTAG AGAATGCACA    3109
GGTGTTGGTG AGGGCGTGTG GCTGAGCACT ACATGTCAAG TCAGAGTCAG TTTCTATCCA    3169
ATTCTC                                                              3175
```

( 2 ) INFORMATION FOR SEQ ID NO:2:

( i ) SEQUENCE CHARACTERISTICS:
        ( A ) LENGTH: 652 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

|  |  |  |  |  |  |  |  |  |  |  |  |  |  |  |
|---|---|---|---|---|---|---|---|---|---|---|---|---|---|---|
| Met 1 | Ala | Met | Asp | Glu 5 | Tyr | Leu | Trp | Met | Val 10 | Ile | Leu | Gly | Phe | Ile Ile 15 |
| Ala | Phe | Ile | Leu 20 | Ala | Phe | Ser | Val | Gly 25 | Ala | Asn | Asp | Val | Ala 30 | Asn Ser |
| Phe | Gly | Thr 35 | Ala | Val | Gly | Ser | Gly 40 | Val | Val | Thr | Leu | Arg 45 | Gln | Ala Cys |
| Ile | Leu 50 | Ala | Ser | Ile | Phe | Glu 55 | Thr | Thr | Gly | Ser | Val 60 | Leu | Leu | Gly Ala |
| Lys 65 | Val | Gly | Glu | Thr | Ile 70 | Arg | Lys | Gly | Ile | Ile 75 | Asp | Val | Asn | Leu Tyr 80 |

```
Asn  Glu  Thr  Val  Glu  Thr  Leu  Met  Ala  Gly  Glu  Val  Ser  Ala  Met  Val
               85                      90                      95

Gly  Ser  Ala  Val  Trp  Gln  Leu  Ile  Ala  Ser  Phe  Leu  Arg  Leu  Pro  Ile
              100                     105                     110

Ser  Gly  Thr  His  Cys  Ile  Val  Gly  Ser  Thr  Ile  Gly  Phe  Ser  Leu  Val
              115                     120                     125

Ala  Ile  Gly  Thr  Lys  Gly  Val  Gln  Trp  Met  Glu  Leu  Val  Lys  Ile  Val
         130                     135                     140

Ala  Ser  Trp  Phe  Ile  Ser  Pro  Leu  Leu  Ser  Gly  Phe  Met  Ser  Gly  Leu
145                     150                     155                          160

Leu  Phe  Val  Leu  Ile  Arg  Ile  Phe  Ile  Leu  Lys  Lys  Glu  Asp  Pro  Val
              165                     170                     175

Pro  Asn  Gly  Leu  Arg  Ala  Leu  Pro  Val  Phe  Tyr  Ala  Ala  Thr  Ile  Ala
              180                     185                     190

Ile  Asn  Val  Phe  Ser  Ile  Met  Tyr  Thr  Gly  Ala  Pro  Val  Leu  Gly  Leu
              195                     200                     205

Val  Leu  Pro  Met  Trp  Ala  Ile  Ala  Leu  Ile  Ser  Phe  Gly  Val  Ala  Leu
     210                     215                     220

Leu  Phe  Ala  Phe  Phe  Val  Trp  Leu  Phe  Val  Cys  Pro  Trp  Met  Arg  Arg
225                     230                     235                          240

Lys  Ile  Thr  Gly  Lys  Leu  Gln  Lys  Glu  Gly  Ala  Leu  Ser  Arg  Val  Ser
              245                     250                     255

Asp  Glu  Ser  Leu  Ser  Lys  Val  Gln  Glu  Ala  Glu  Ser  Pro  Val  Phe  Lys
              260                     265                     270

Glu  Leu  Pro  Gly  Ala  Lys  Ala  Asn  Asp  Ser  Thr  Ile  Pro  Leu  Thr
         275                     280                     285

Gly  Ala  Ala  Gly  Glu  Thr  Leu  Gly  Thr  Ser  Glu  Gly  Thr  Ser  Ala  Gly
     290                     295                     300

Ser  His  Pro  Arg  Ala  Ala  Tyr  Gly  Arg  Ala  Leu  Ser  Met  Thr  His  Gly
305                     310                     315                          320

Ser  Val  Lys  Ser  Pro  Ile  Ser  Asn  Gly  Thr  Phe  Gly  Phe  Asp  Gly  His
              325                     330                     335

Thr  Arg  Ser  Asp  Gly  His  Val  Tyr  His  Thr  Val  His  Lys  Asp  Ser  Gly
              340                     345                     350

Leu  Tyr  Lys  Asp  Leu  Leu  His  Lys  Ile  His  Ile  Asp  Arg  Gly  Pro  Glu
              355                     360                     365

Glu  Lys  Pro  Ala  Gln  Glu  Ser  Asn  Tyr  Arg  Leu  Leu  Arg  Arg  Asn  Asn
     370                     375                     380

Ser  Tyr  Thr  Cys  Tyr  Thr  Ala  Ala  Ile  Cys  Gly  Leu  Pro  Val  His  Ala
385                     390                     395                          400

Thr  Phe  Arg  Ala  Ala  Asp  Ser  Ser  Ala  Pro  Glu  Asp  Ser  Glu  Lys  Leu
              405                     410                     415

Val  Gly  Asp  Thr  Val  Ser  Tyr  Ser  Lys  Lys  Arg  Leu  Arg  Tyr  Asp  Ser
              420                     425                     430

Tyr  Ser  Ser  Tyr  Cys  Asn  Ala  Val  Ala  Glu  Ala  Glu  Ile  Glu  Ala  Glu
          435                     440                     445

Glu  Gly  Gly  Val  Glu  Met  Lys  Leu  Ala  Ser  Glu  Leu  Ala  Asp  Pro  Asp
     450                     455                     460

Gln  Pro  Arg  Glu  Asp  Pro  Ala  Glu  Glu  Lys  Glu  Glu  Lys  Asp  Ala
465                     470                     475                          480

Pro  Glu  Val  His  Leu  Leu  Phe  His  Phe  Leu  Gln  Val  Leu  Thr  Ala  Cys
              485                     490                     495

Phe  Gly  Ser  Phe  Ala  His  Gly  Gly  Asn  Asp  Val  Ser  Asn  Ala  Ile  Gly
              500                     505                     510
```

```
Pro  Leu  Val  Ala  Leu  Trp  Leu  Ile  Tyr  Lys  Gln  Gly  Gly  Val  Thr  Gln
          515                      520                     525

Glu  Ala  Ala  Thr  Pro  Val  Trp  Leu  Leu  Phe  Tyr  Gly  Gly  Val  Gly  Ile
     530                      535                     540

Cys  Thr  Gly  Leu  Trp  Val  Trp  Gly  Arg  Arg  Val  Ile  Gln  Thr  Met  Gly
545                      550                     555                          560

Lys  Asp  Leu  Thr  Pro  Ile  Thr  Pro  Ser  Ser  Gly  Phe  Thr  Ile  Glu  Leu
                565                          570                          575

Ala  Ser  Ala  Phe  Thr  Val  Val  Ile  Ala  Ser  Asn  Ile  Gly  Leu  Pro  Val
               580                    585                          590

Ser  Thr  Thr  His  Cys  Lys  Val  Gly  Ser  Val  Val  Ala  Val  Gly  Trp  Ile
          595                      600                     605

Arg  Ser  Arg  Lys  Ala  Val  Asp  Trp  Arg  Leu  Phe  Arg  Asn  Ile  Phe  Val
     610                      615                     620

Ala  Trp  Phe  Val  Thr  Val  Pro  Val  Ala  Gly  Leu  Phe  Ser  Ala  Ala  Val
625                      630                     635                          640

Met  Ala  Leu  Leu  Met  Tyr  Gly  Ile  Leu  Pro  Tyr  Val
                645                    650
```

NUCLEIC ACID MOLECULE ENCODING THE AMPHOTROPIC VIRUS RECEPTOR

Following the discovery of human immunodeficiency virus and human T-cell leukemia virus, the study of unrecognized frequent infection of humans and other mammals by retroviruses has been more actively studied. Of particular interest is the study of how retroviruses achieve infection. It is generally understood that the initial stage of infection requires an interaction between a glycoprotein of the retrovirus envelope and a receptor on the surface of the intended host's cells. It is known that different retroviruses utilize different receptors in infecting host cells, and the absence of the appropriate retroviral receptor on the cell of a particular species will prevent infection by that retrovirus. Interference studies indicate that there are probably no more than eight different retrovirus receptors for retroviruses known to infect human cells (Sommerfelt and Weiss, Virology, 176:58–69, 1990). Many retroviruses can infect human cells in vitro, but the role of such viruses in causing disease, if any, has yet to be elucidated. The study of the retrovirus life cycle is hampered by a lack of knowledge of the identity and structure of the various retroviral receptors, and the extent of their expression in human and other potential host cells.

One recently identified receptor is that for Gibbon Ape Leukemia Virus (GALV; U.S. Pat. No. 5,151,361). GALV is known to cause myeloid leukemias in gibbons, and has been isolated from animals with lymphosarcoma and granulocyte leukemia (Kawakamira and Buckley, Transplant Proc., 6:193–196, 1984; Kawakami et al., Nature (London) New Biol., 235:170–171, 1972, Kawakami et al., Int. J. Cancer, 25:841–846, 1980). Although there is no known disease caused by this virus in humans, its receptor (GLVR1) is expressed in human cells. In addition to acting as the receptor for GALV, this receptor is also utilized by another retrovirus, Feline Leukemia Virus-B (FeLV-B).

It has now been unexpectedly determined that a gene highly homologous, but not identical, to the GALV receptor exists. This gene is designated as GLVR2. Most surprisingly, however, the gene is determined to encode yet another functionally distinct retroviral receptor, namely the receptor for amphotropic retroviruses. Amphotropic retroviruses comprise a distinct group of murine viruses with a wide host range. They infect most mammalian cells, including human.

SUMMARY OF THE INVENTION

The present invention provides an isolated nucleic acid fragment comprising a nucleic acid sequence encoding an amphotropic retrovirus receptor, hereinafter referred to as GLVR2, and is approximately 62% homologous to the GLVR1 gene that encodes the GALV receptor. However, the two receptors encoded by the different genes are sufficiently distinct so as to serve as receptors for different types of retroviruses. It is determined that GALV cannot use GLVR2 as a receptor, that is, mouse NIH 3T3 cells transfected with an expression plasmid for GLVR2 cannot be infected with GALV, whereas Chinese hamster ovary cells transfected with the same plasmid become infectable with amphotropic virus. Similarly, given this observation, it is expected that amphotropic virus will be unable to use GLVR1 as a receptor, because the receptors map to physically distinct locations in the human genome (Kaelbling et al., J. Virol., 65:1743–1747, 1991; Garcia et al., J. Virol., 65:6316–6319, 1991) and because the viruses do not interfere in human cells (Sommerfelt and Weiss, Virology, 176:58–69, 1990).

The fragment can also be used to create vectors for transformation of host cells to express the GLVR2 gene and receptor protein. The invention also provides probes, in the form of the nucleic acid fragment or portions thereof, which have been detectably labelled, Such probes are useful in the study of receptor distribution in cells of various species and/or tissue types. Amphotropic virus vectors are currently the standard for human gene therapy. Determination of the levels of GLVR2 expression in target cells or tissues is therefore useful in assessing the potential for successful gene delivery. Comparison to GLVR1 levels is useful in deciding which of the two vector systems should be used. As demonstrated here by the isolation of GLVR2 using GLVR1 as a probe in low stringency screening of recombinant libraries, both GLVR1 and -2 are useful for the isolation of further GLVR-like sequences from various species.

Also provided are recombinantly expressed amphotropic receptor proteins, and antibodies raised thereto.

BRIEF DESCRIPTION OF THE FIGURES

FIG. 1 shows the DNA sequence of GLVR2 cDNA (a composite of clones 1 and 9SEQ ID NO: 1). The ATG and TGA delineating the open reading frame homologous to GLVR1 are underlined.

FIG. 2 shows the amino acid sequence encoded by the cDNA depicted in FIG. 1 hereinafter SEQ ID NO; 2.

DETAILED DESCRIPTION OF THE INVENTION

Four hundred thousand plaques from a human HL60 cell cDNA library are screened under low stringency conditions with a cDNA fragment containing the human GLVR1 sequence. After two washes, about 20 positive plaques are picked and purified. Two clones are identified as containing GLVR1 related sequence, but neither clone contains a full-length coding region. An additional 350,000 plaques from a human placenta cDNA library are screened under high stringency condition. An additional eight plaques are identified. Digestion of rescued plasmids shows inserts ranging from 0.6–3.7 kb. A larger clone (about 2.? kb) is sequenced and found to be missing about 0.5 kb of the 5', coding sequence relative to the GLVR1 sequence. The cDNA library is again screened with a 300 bp fragment of this positive clone at high stringency, resulting in 9 clones, at least one of which contains a full GLVR2 sequence homologous to the GLVR1 open reading frame. The isolated clone is approximately 5.5 kb, with an open reading frame of 1956 bases, producing a full-length protein of 652 amino acids in length. The nucleotide and amino acid sequence are depicted respectively in FIGS. 1 and 2. The identity of the gene as encoding an amphotropic virus receptor is confirmed by the observation that CHO cells, which are normally resistant to infection by murine amphotropic virus, upon transfection with a GLVR2 containing vector, become infectable.

The conclusively identified clone is then used in Southern hybridization to identify the presence of homologues in DNA derived from other species. Homologous genes are shown to be present in monkey, rat, dog, cow, rabbit and chicken, but not in yeast cells.

Southern analysis of a panel of human-mouse hybrid cells is used to map the chromosomal location of GLVR2. This procedure shows that GLVR2 maps to human chromosome 8, in contrast with GLVR1, which maps to human chromosome 2.

The novel nucleic acid fragments provide a useful tool for the study of retroviruses. The fragment encoding the receptor, or portions thereof, can be detectably labelled (e.g., with a radioisotope) and used as a probe to identify and isolate GLVR2 homologues from a variety of species. This can be readily achieved by screening genomic or cDNA libraries under conditions of low stringency and thereby isolating novel GLVR-related sequences. If these clones do not encode full-length GLVR proteins, they can be used as probes in turn to isolate full-length clones. Therefore, the "isolated nucleic acid fragment" claimed herein also is intended to encompass nucleic acid fragments which hybridize with a nucleic acid sequence encoding the amino acid sequence of FIG. 2, wherein the nucleic acid fragment encodes a functional amphotropic receptor. By encoding a functional receptor, it is meant that when transfected into a cell previously resistant to amphotropic virus infection, the cell is thereby rendered infectable.

Isolated GLVR2 fragments can be used to express the receptor in a variety of host cells, both prokaryotic and eukaryotic. Examples of suitable eukaryotic cells include mammalian cells, plant cells, yeast cells, and insect cells. Suitable prokaryotic hosts include *Escherichia coli* and *Bacillus subtilis*.

Suitable expression vectors are selected based upon the choice of host cell. Numerous vectors suitable for use in transforming bacterial cells are well known. For example, plasmids and bacteriophages, such as λ phage, are the most commonly used vectors for bacterial hosts, and for *E. coli* in particular. In both mammalian and insect cells, virus vectors are frequently used to obtain expression of exogenous DNA. In particular mammalian cells are commonly transformed with SV40, polyoma virus, or transfected with plasmids such as pRC/CNV; and insect cells in culture may be transformed with baculovirus expression vectors. Yeast vector systems include yeast centromere plasmids, yeast episomal plasmids and yeast integrating plasmids. The invention encompasses any and all host cells transformed or transfected by the claimed nucleic acid fragments, as well as expression vectors used to achieve this.

In one specific application, the receptor DNA can be expressed in cell lines normally resistant to infection by a particular retrovirus. The transfected cell is then contacted with that retrovirus, to determine if it has been rendered infectable. If infection is achieved after transfection, GLVR2 will have been demonstrated to encode the receptor for that virus.

In another embodiment, the receptor gene is used to express the protein in a bacterial host. Protein expressed in bacteria can be used in raising antisera (both polyclonal and monoclonal) by standard methodology. Such antibodies are useful in immunohistochemical studies to determine the level of expression of the receptor protein in various tissues and cell lines. The receptor can be purified from bacterial cells if found in inclusion bodies, for example, by isolation of inclusion bodies by standard techniques, followed by electrophoresis in SDS-PAGE gels and isolation of the protein band from the gel. Alternately, the long hydrophilic region (residues 236–482 in the human protein) can be expressed as a fusion protein, e.g., with glutathione-s-transferase, or maltose binding protein, and then purified by isolation of the protein to which it is fused.

Alternately, the predicted amino acid sequence can be used to design synthetic peptides unique to the amphotropic receptor, which peptides can then be used to raise antibodies to the receptors.

Amphotropic virus vectors are currently the only ones used for human gene therapy. Knowledge of expression levels for the amphotropic receptor is therefore important. Isolation of the receptor may lead to a better understanding of how the virus and receptor interact and may lead to improved modalities for gene therapy.

Also, the nucleic acid fragment, or portions thereof, can be used as a probe to isolate other genes in the GLVR family. The data provided herein demonstrate that there is more than one GLVR gene, and given this observation, it is predicted that GLVR genes other than GLVR1 and 2 also exist. In particular, since the envelope glycoprotein of xenotropic retroviruses is homologous to the amphotropic and FeLV-B envelope glycoprotein, but these viruses do not use the same receptors, the homology suggests the use of a receptor homologous to GLVR1 and 2. Thus, the predicted xenotropic virus receptor, herein designated GLVR3, can be isolated using either GLVR1 or 2 as a probe, in the same manner as described herein for GLVR2 isolation. Identity of isolated clones can be confirmed by sequencing and expression also described herein.

It will be understood by those skilled in the art that the invention is not limited to the specific nucleotide and amino acid sequences depicted in FIGS. 1 and 2 SEQ. ID NO: 2, respectively: in addition to the human GLVR2 sequence depicted therein, the invention also encompasses modifications to the sequence, such as deletions, insertions, or substitutions in the sequence which produce silent changes in the resulting protein molecule. For example, alteration in the gene sequence which reflect the degeneracy of the genetic code, or which result in the production of a chemically equivalent amino acid at a given site, are contemplated; thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a biologically equivalent product. Nucleotide changes which result in alteration of the N-terminal and C-terminal portions of the protein molecule would also not be expected to alter the activity of the protein. It may also be desirable to eliminate one or more of the cysteines present in the sequence, as the presence of cysteines may result in the undesirable formation of multimers when the protein is produced recombinantly, thereby complicating the purification and crystallization processes. In some cases, it may in fact be desirable to make mutants of the sequence in order to study the effect of alteration on the biological activity of the protein. Each of the proposed modifications is well within the routine skill in the art, as is determination of retention of biological activity of the encoded products.

The invention is further described in the following non-limiting examples.

EXAMPLES

1. Isolation of cDNAs for GLVR2

400,000 plaques from a human cDNA library made from HL60 cells (Clontech #1020b) are screened at low stringency with two EcoRI fragments containing bases 1-2659 for the human GLVR1 cDNA-containing clone pHGR6-1 (O'Hara et al., 1990). The screening is carried out in 50% formamide, 5× SSC, 10× Denhardt's 0 1% SDS, and 100

μg/ml salmon sperm DNA, at 30° C. The filters are washed in 0.2× SSC, 0.2% SDS at 45° C. for 20 minutes and exposed to film for 3 days. The filters are then rewashed in the same solution at 65° C. for 30 minutes and exposed to film. About 40 plaques are detected after the first wash, but only about 20 after the second. The first set of plaques are picked and plaque-purified using the less stringent conditions. Two clones, OJ40A and OJ40B, make it through this procedure and contain GLVR1-related sequences as determined by DNA sequencing. Because these clones contain only several hundred bases related to the GLVR1 codon region, efforts are made to isolate full-length clones. To do this, 350,000 plaques from a human placenta cDNA library (Stratagene, 936203) are screened using a 1kb BamHI fragment of OJ40B at high stringency (hybridization is in the above hybridization solution at 42° C.; washing is at a final stringency of 0.2% SDS, 0.2× SSC, 65° C.). The eight positive plaques are rescued from the λzap vector using the manufacturer's protocol. EcoRI digests of the rescued plasmids reveal insert sizes ranging from 0.6–3.7 kb. One of the largest clones (#9, ~2.7 kb) is sequenced in its entirety using synthetic primers and the dideoxy chain termination method on double stranded templates (Sanger et al., PNAS USA, 74:5463–5467, 1977). Compared to GLVR1 sequence, this clone is missing 0.5 kb of the 5', coding sequence. The cDNA library is then screened with the 5' 300 bp HindIII-NcoI fragment of clone 9 at high stringency, resulting in 9 clones, at least one of which contains the full GLVR2 sequence homologous to the open reading frame of GLVR1 (clone 1, 5.5 kb).

2. Southern Analysis

A Southern blot (containing DNAs from various species and purchased from Clontech) is hybridized in the hybridization solution described above at 30° C. with the HindIII-NcoI fragment of clone 1 as probe. The blot is washed at a final stringency of 0.2% SDS, 0.2× SSC at 40° C. The result shows the presence of a homologous gene in monkey, rat, dog, cow, rabbit, and chicken, but not in yeast.

3. Chromosomal mapping of GLVR2

The chromosomal location of GLVR2 is determined using Southern Analysis of a panel of human-mouse hybrid cells (which tend to lose human chromosomes with time in culture) and the 1 kb BamHI fragment of pOJ40B as probe. In this widely used system, described in Kaelbling et al. (J. Virology, 65:1743–1747, 1991), hybrids are first characterized cytogenetically for which human chromosomes they contain. Southern analysis is then used to determine which of the hybrids carry the gene being mapped. A table is then drawn up showing concordance between the presence of the gene and the presence of a specific human chromosome. In this way, GLVR2 is shown to map to human chromosome 8.

4. Expression of GLVR2

In order to construct an expression plasmid for GLVR2, the following steps are taken. pcDNA-tkpA, constructed by Dr. Tom Jones, Lederle Laboraroties, is derived from pcDNA1 (In Vitrogen). For convenience in manipulation, the ampicillin resistance gene is cloned into pcDNA1 by cloning in a blunt 1.1kb fragment from pBR322 encoding $Amp^R$ into the NruI site of pcDNA1 between supF and the cytomegalovirus (CMV) immediate early promoter. The 1.23kb XbaI-AccI fragment (containing the splice, polyadenylation signal, and SP6 promoter) is removed, the vector filled in with Klenow, and a 180 bp BamHI-HaeIII fragment (filled in with Klenow) containing the Herpes simplex virus thymidine kinase polyadenylation signal, is inserted. To clone GLVR2 into this plasmid, the HindIII-SacI fragment of pGLVR2-1 (nucleotides 184–2745 in FIG. 1 SEQ ID NO; 1, containing the complete open reading frame with 59 untranslated nucleotides upstream of the open reading frame and 543 untranslated nucleotides downstream of the open reading frame) is cloned between the HindIII and EcoRV sites of pcDNA1-tkpA. The clone is designated pOJ74. This clone, when introduced into Chinese hamster ovary cells, confers susceptibility to infection by recombinant retroviruses with murine leukemia virus gag-pol proteins and amphotropic envelope glycoprotein. Susceptibility is conferred by relieving a receptor block because the same (untransfected) cells are normally infectable by a virus with the same gag-pol proteins, but containing gibbon ape leukemia virus envelope glycoprotein.

DEPOSIT OF BIOLOGICAL MATERIALS

The following biological materials have been deposited with the American Type Culture Collection, 12301 Parklawn Drive, Rockville, Md., under the Budapest Treaty, on Apr. 1, 1993 and given the indicated Accession Numbers:

| Description | Accession No. |
|---|---|
| pOJ74/E. coli DH5α (containing GLVR2) | ATCC 69274 |

What we claim is:

1. A purified, isolated nucleic acid molecule encoding the amino acid sequence set forth in SEQ ID NO: 2.

2. A recombinant vector comprising a purified, isolated nucleic acid molecule as defined in claim 1.

3. A host cell comprising a vector as defined in claim 2.

4. A host cell as defined in claim 3, wherein said host cell prior to said transformation, is not infectable by an amphotropic retrovirus.

5. A purified, isolated nucleic acid molecule comprising the sequence set forth in SEQ ID NO: 1.

6. A recombinant vector comprising a purified, isolated nucleic acid molecule as defined in claim 5.

7. A host cell transformed with a vector as defined in claim 6.

8. A host cell as defined in claim 7, wherein said host cell, prior to said transformation, is not infectable by an amphotropic retrovirus.

* * * * *

UNITED STATES PATENT AND TRADEMARK OFFICE
CERTIFICATE OF CORRECTION

PATENT NO. : 5,550,221
DATED : August 27, 1996
INVENTOR(S) : Stephen V. Johann, et al.

It is certified that error appears in the above-identified patent and that said Letters Patent is hereby corrected as shown below:

Col. 2, line 43: change "(about 2.? kb)" to --(about 2.7 kb)--.

Col. 2, line 22: change " Figure 1 shows" to --Figures 1A and 1B show--.

Col. 2, line 23: change "9SEQ" to -- 9 hereinafter SEQ--.

Col. 2, line 53: change "Figure 1" to --Figures 1A and 1B--.

Col. 4, line 24: change "FIGS. 1" TO --FIGS. 1A, 1B; same line: insert --SEQ. ID NO: 1 and-- before "SEQ. ID NO: 2, respectively".

Col. 6, line 21: change "FIG. 1" to --FIGS. 1A and 1B.

Col. 6, line 9: change "Laboraroties" to --Laboratories--.

Signed and Sealed this

Seventh Day of December, 1999

Attest:

Q. TODD DICKINSON

*Attesting Officer*  *Acting Commissioner of Patents and Trademarks*